United States Patent
Thelen

[19]
[11] Patent Number: 6,112,573
[45] Date of Patent: Sep. 5, 2000

[54] PROCESS FOR DETERMINING THE LUBRICANT POWER OF LUBRICANT OILS

[75] Inventor: Edgar Thelen, Friedrichshafen, Germany

[73] Assignee: ZF Friedrichshafen AG, Friedrichshafen, Germany

[21] Appl. No.: 09/284,356

[22] PCT Filed: Oct. 25, 1997

[86] PCT No.: PCT/EP97/05904

§ 371 Date: Apr. 12, 1999

§ 102(e) Date: Apr. 12, 1999

[87] PCT Pub. No.: WO98/19157

PCT Pub. Date: May 7, 1998

[30] Foreign Application Priority Data

Oct. 31, 1996 [DE] Germany .......................... 196 44 029

[51] Int. Cl.[7] .................................................. G01N 19/02
[52] U.S. Cl. .................................................. 73/10
[58] Field of Search ................................. 73/10, 53.05

[56] References Cited

U.S. PATENT DOCUMENTS

| | | | |
|---|---|---|---|
| 2,909,056 | 10/1959 | Neely | 73/10 |
| 3,045,471 | 7/1962 | Chapman et al. | 73/10 |
| 3,913,377 | 10/1975 | Lindeman | 73/10 |

FOREIGN PATENT DOCUMENTS

| | | |
|---|---|---|
| 2 277 342 | 1/1976 | France . |
| 28 31 158 C2 | 1/1980 | Germany . |
| 84 28 799 | 11/1984 | Germany . |
| 2 65 693 A1 | 3/1989 | Germany . |
| 39 33 973 A1 | 4/1991 | Germany . |
| 3 01 700 A9 | 5/1992 | Germany . |
| 1511635 | 9/1989 | U.S.S.R. .................................... 73/10 |

OTHER PUBLICATIONS

Japanese Abstract No. 2–247542 A, P–1145, Dec. 20, 1990, vol. 14, No. 574 issued to Hitachi Seiki Co. Ltd.

*Primary Examiner*—Robert Raevis
*Attorney, Agent, or Firm*—Davis and Bujold

[57] ABSTRACT

A process for determining the lubricant power of lubricant oils for slip-controlled clutches. In a test container (14) consisting of a double-walled, temperable vessel and filled with test lubricant oil, two friction partners (6, 8) are rotated against each other under a test load with practical conditions. A coefficient of friction characteristic curve (27, 28) is determined depending on the sliding speed. If in a working range (26) a progressive characteristic curve is obtained, the lubricant oil is suitable for use in slip-controlled clutches. Since the device required to carry out the process has a relatively simple structure and requires only a small amount of test lubricant oil, the process and device can be used to test production charges in lubricant oil development, during test bench or field tests and to test aging processes in a laboratory.

1 Claim, 2 Drawing Sheets

PROCESS FOR DETERMINING THE LUBRICANT POWER OF LUBRICANT OILS

BACKGROUND OF THE INVENTION

The invention concerns a process for determining the lubricant power of lubricant oils.

The use of lubricant oils, especially lubricant oils called "automatic transmission fluids" (ATF), in a slip-controlled clutch presupposes accurate knowledge of the friction value curve as a function of the sliding speed. If, in the operating range the curve of the friction value, dependent on the sliding speed, does not correspond to a progressive curve, it is thus expected that self-exciting friction oscillations will occur in the vehicle. Thus, there is no longer an orderly working of slip-controlled clutches, for example, in regulated converter lock-up clutches.

As a rule, lubricant oils are evaluated, with regard to their fitness for use in slip-controlled clutches, by costly test bench superstructures with original installation parts. The values obtained, of course, should not be assigned at once to the lubricant power, rather, but not until after a certain service life of the lubricant oils. Further tests at regular intervals are needed, but not reasonably possible in cost and time spent. For the same reasons, a widespread analysis in vehicle and/or components tests is mostly eliminated. But the knowledge of these values is indispensable when a long-term fitness for lubricant oils must be guaranteed.

The invention is based on the problem of providing a process and a device with which the lubricant power of lubricant oils for slip-controlled clutches can be determined at a low cost so that decisive statements about a long-term fitness are possible.

SUMMARY OF THE INVENTION

No original installation parts are needed for the process and device according to the invention. Besides, only small quantities of oil, about 100 ml, are required. Thereby, resulting in savings of cost and time in relation to both the test bench structure and the performance of the test. Thus, the lubricant power can now be detected together with vehicle or test bench tests, since only a small fragment of the lubricant oil is removed from the lubricant oil circuit for testing purposes and the residual lubricant oil remains in the long-term test.

The amount of test oil is conveniently limited to less than 200 ml. In addition, the test container and the parts contained therein, such as the specimen holder, etc., can be dimensioned accordingly so that even with small amounts of test oil the contact surfaces are always sufficiently supplied with test oil during the test. It is also possible to situate additional displacement bodies in the test container in order to obtain the desired amount of test oil. For the development of adequate lubricant oils, it is of decisive importance to know the change of the friction value characteristic as a function of the service life. With the process and corresponding device, according to the invention, it is possible to describe friction systems, such as existing in slip-controlled clutches, in relation to their coefficient of friction characteristic curve in different states of processing and utilization. The process and device thus can be used in lubricants for control of production charges in lubricant oil development during test bench or field tests, to test aging processes in a laboratory and for evaluating new friction surfaces.

In the specification and in the claims, numerous features are shown and described in combination. The expert will conveniently consider the combined features also individually, depending on the problems to be solved, and form convenient added combinations.

BRIEF DESCRIPTION OF THE DRAWING(S)

An embodiment of the invention is shown in the drawing in which:

FIG. 1 diagrammatically shows a structure of a device according to the invention;

DESCRIPTION OF THE PREFERRED EMBODIMENT(S)

Figure 1:
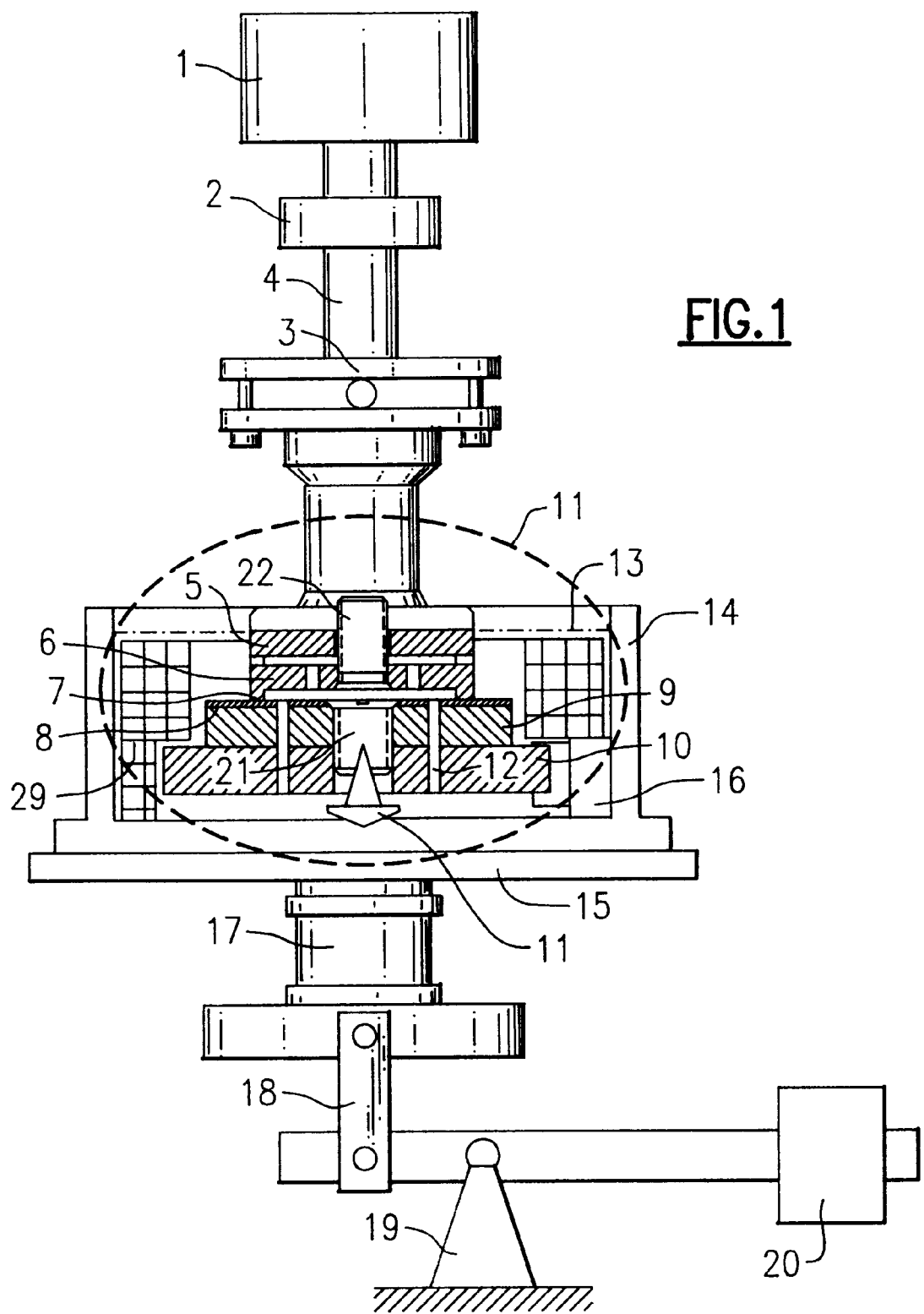
Figure 2:
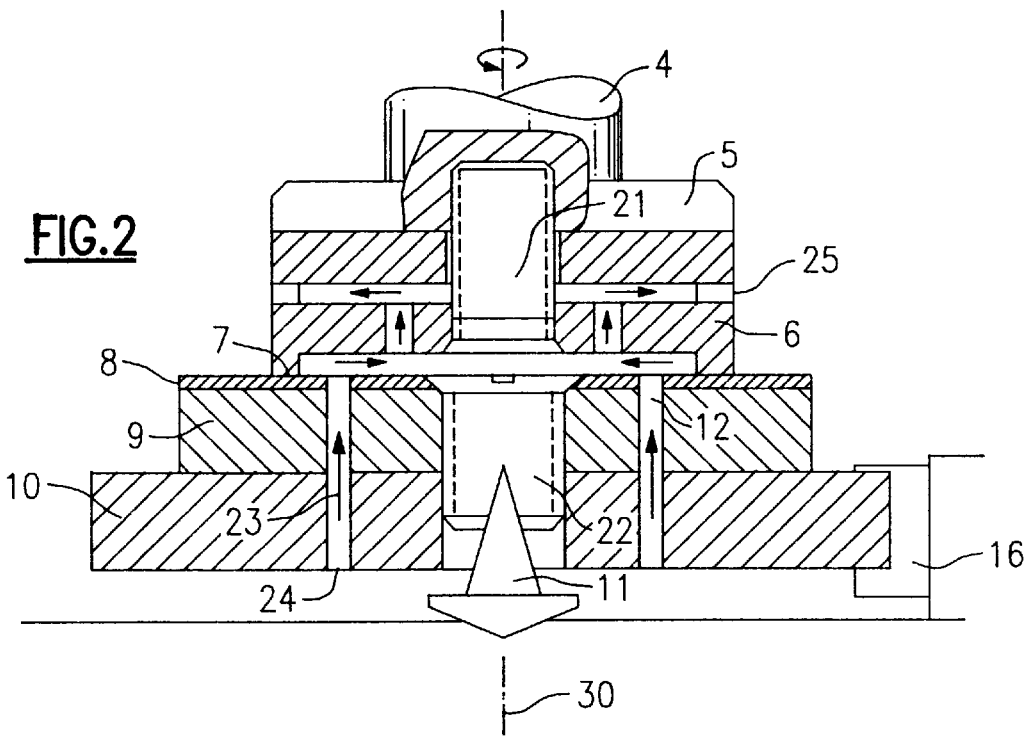
FIG. 2 shows in enlarged view a range II in FIG. 1.

A motor 1 drives, via a torque indicator 2, an input shaft 4, an equalizer connection 3, and a thrust washer 5 on which a ring disc 6 is fastened with a bolt 22. The ring disc 6 forms a friction partner and has a ring surface 7 with which it abuts on another friction part. The latter is formed by a friction lining 8 which is superimposed on a main body 9. The main body 9 is screwed by means of a bolt 21 with a specimen holder 10 which is non-rotatably retained in a test container 14 by a torque support 16 and is supported tiltably towards all sides by a peak bearing 11. Instead of the peak bearing 11, which is formed by a double taper body, there can also be used a ball which meshes in corresponding calottes of the adjacent parts.

The test container 14 is double walled and can be tempered so that lubricant oils and friction pairs can be tested at different working temperatures. It is filled with test oil up to an oil level designated with 13.

The test container 14 rests on a test board 15. A load delivery system 20 presses the test board 15 with the test container 10, the main body 9 and the friction lining 8 against the ring surface 7 of the ring disc 6, via a lever mechanism 18, which flexibly supports itself on a foundation 19.

The process, according to the invention, is carried out as follows:

The two friction partners formed by the ring disc 6 on one side and the main body 9 with the friction lining 8 on the other are clamped and then the test container 14 is filled with the test oil that is to be tested. Both friction parts essentially correspond to the friction pairs used in practice. To test the friction pairs for the long-term fitness thereof, a reliable test oil of known properties is used as the test oil.

The alignment of the measured value sensors thus follows. To measure the normal force, a dynamometer device 17 is integrated in the force flow, for example, as shown in FIG. 1, between the lever mechanism 18 and the test board 15. The friction force is determined by means of a strain gauge on the torque support 16. The input torque of the motor 1, which is regulated by an external theoretical value transmitter on a preset theoretical speed, can be detected by means of the torque indicator 2 and alternatively used to determine, even though with less accuracy, the friction force. Thereafter the test load is applied, which by virtue of the peak bearing 11 and the connection 3, is distributed evenly over the ring surface 7.

With a double-walled, temperature controllable vessel as the test container 14, for which serves a temperature sensor, not shown, the test temperature can be adjusted in the test container 14. When the test temperature is reached, the introductory operation to form the friction surfaces on the ring surface 7 and on the friction lining 8 can be started. This is followed by the actual test cycle, wherein carried out is a series of measurements with several sliding speeds which have been reset by the theoretical speed of the motor 1. The friction value is mathematically determined from the ratio of the friction force to normal force.

Members 29 may be provided to displace a portion of the oil being tested thereby to reduce the volume of the oil in the container 14.

Figure 3:
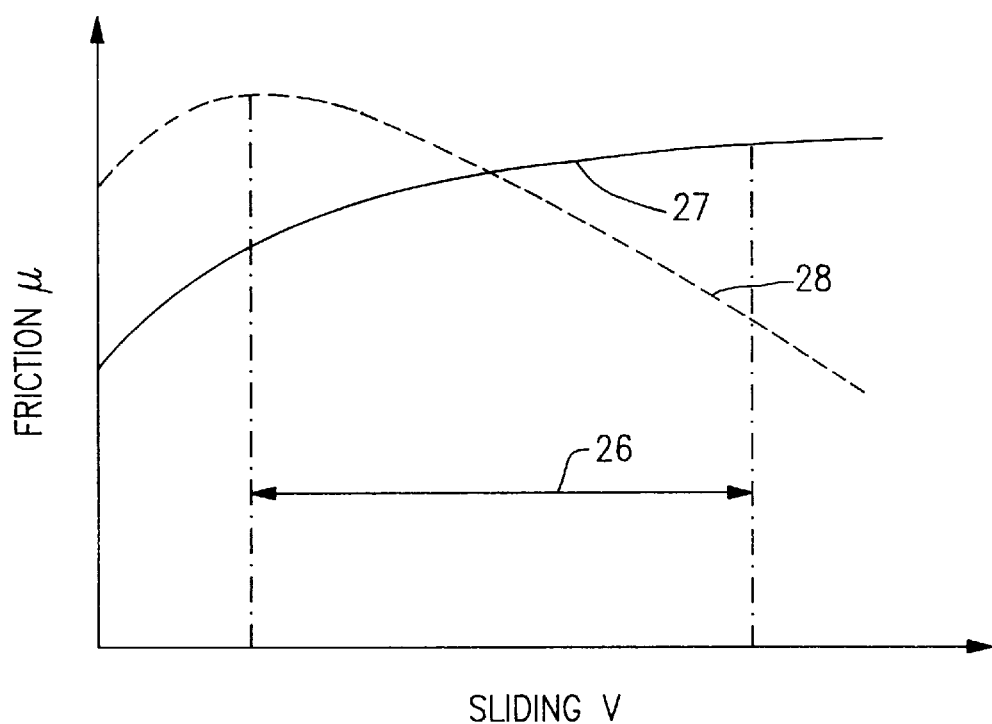
FIG. 3 shows the coefficient of friction characteristic curves.

FIG. 3 shows a diagram with two coefficient of friction characteristic curve 27 and 28. If the coefficient of friction characteristic curve 27 extends progressively in a working range 26, the lubricant is suitable for use in slip-controlled clutches. But if the friction characteristic value 28 progressively drops, self-excited oscillations are to be expected in the use of the vehicle so that the lubricant is inadequate for use in this case.

To prevent the test oil from overheating under the ring disc 6, which on the contrary remains at a uniform temperature, there are provided in the specimen holder 10 and in the main body 9, as well as, in the ring disc 6 and the thrust washer 5, oil ducts 12 through which the test oil is circulated in direction of the arrow 23 from an oil inlet 24 to an oil outlet 25. The circulation effect is produced by centrifugal force in the parts of the rotary oil ducts 12 which extend substantially radially.

Owing to the simple structure and the small amount of test oil required for a measured value series, the expense for the measurements can be kept within reasonable limits during a service life cycle. The small test oil removal allows fatigue tests to be continued without impairment so that measurement results of assertive force are obtained for the entire service cycle.

| Reference numerals |
|---|
| 1 motor |
| 2 torque indicator |
| 3 equalizer connection |
| 4 input shaft |
| 5 thrust washer |
| 6 ring disc |
| 7 ring surface |
| 8 fiction lining |
| 9 main body |
| 10 specimen holder |
| 11 peak bearing |
| 12 oil ducts |
| 13 oil level |
| 14 test container |
| 15 test board |
| 16 torque support |
| 17 dynamometer device |
| 18 lever mechanisrn |
| 19 foundation |
| 20 load delivery system |
| 21 bolt |
| 22 bolt |
| 23 arrow |
| 24 oil inlet |
| 25 oil outlet |
| 26 working range |
| 27 friction characteristic curve |
| 28 friction characteristic curve |
| 29 displacement body |
| 30 axis |

What is claimed is:

1. A process of ascertaining the lubricant power of lubricant in controlled slip clutches, comprising the steps of:

a) providing a test device comprising a test container (14) in which is a first member (6) rotatable by a motor (1) relative to a second member (9), the second member (9) being non-rotatably supported in the container (14) on a bearing (11) and abutting the first member (6) at an annular friction interface (7, 8), and a load delivery system (18, 19, 20) for urging the second member (9) and the first member (6) into mutual engagement at the interface (7, 8);

b) placing a quantity of test oil in the container (14) to immerse at least the second member (9) and the interface (7, 8);

c) applying a test load to the second member (9) to urge the second member (9) into engagement with the first member (6) at the interface (7, 8) and rotating first member (6) relative to the second member (9);

d) allowing the oil to reach a test temperature;

e) measuring the applied load and torque transmitted by the frictional engagement and calculating therefrom the coefficient of friction of the relatively rotating parts.

* * * * *